US006241688B1

(12) United States Patent
Bouda et al.

(10) Patent No.: US 6,241,688 B1
(45) Date of Patent: Jun. 5, 2001

(54) PORTABLE EQUIPMENT FOR OBTAINING AND ANALYZING RUMINAL LIQUID AND URINE

(75) Inventors: Jan Bouda, Deleg. Coyoacan; Leopoldo Henry Martinez Paasch, Deleg. Alvaro Obregon; Adolfo Kunio Osorio Yabuta, Deleg. Alvaro Obregon; Samuel Genaro Herrera Jardon, Deleg. Alvaro Obregon, all of (MX); Rudolf Dvorak; Jaroslay Doubek, both of Na Morave (CZ)

(73) Assignee: Universidad Nacional Autonoma de Mexico, Coyoacan (MX)

( * ) Notice: Subject to any disclaimer, the term of this patent is extended or adjusted under 35 U.S.C. 154(b) by 0 days.

(21) Appl. No.: 09/142,064

(22) PCT Filed: Feb. 28, 1997

(86) PCT No.: PCT/MX97/00004

§ 371 Date: Dec. 8, 1998

§ 102(e) Date: Dec. 8, 1998

(87) PCT Pub. No.: WO97/31583

PCT Pub. Date: Sep. 4, 1997

(30) Foreign Application Priority Data

Mar. 1, 1996 (MX) .................................................. 960808

(51) Int. Cl.[7] .................................................. A61B 10/00
(52) U.S. Cl. ........................................... 600/573; 119/174
(58) Field of Search .................................. 600/573, 581; 119/174

(56) References Cited

U.S. PATENT DOCUMENTS 3,696,787 * 10/1972 Cooper ................................. 119/174

(List continued on next page.)

FOREIGN PATENT DOCUMENTS 1067176 10/1959 (DE) .

(List continued on next page.)

OTHER PUBLICATIONS

Derwent Abstract of RU 2056944 dated Mar. 27, 1996 (Database WPI Section Ch, Week 9651, London GB).

(List continued on next page.)

Primary Examiner—Eric F. Winakur
Assistant Examiner—Pamela Wingood
(74) Attorney, Agent, or Firm—Ladas & Parry (57) ABSTRACT

The invention reffers to an equipment for collecting and analyzing ruminal fluid and urine, to may possible the diagnosis of ruminants' diseases, as well as the corresponding treatment and prevention. The equipment was designed with the purpose of collecting, in an easy manner, ruminal fluid and urine, to the end of a fast diagnosis be attained and inclusively performing the detection of the cattle's subclinical diseases directly in the field conditions.

The equipment is easy and safe to employ, and facilitates the ruminal fluid applying from a healthy animal to a sick one, as well as the provision of other fluids and drugs directly to the rumen.

The equipment consists of the following instruments:
  a) A tube with metallic head for collecting and applying the fluid to adult bovines.
  b) A tube with metallic head for collecting and applying ruminal fluid to calves and to small ruminants.
  c) A double metallic pump for collecting and applying ruminal fluid and other fluids.
  d) A 5.0-liter-capacity recipient tank for the ruminal fluid collected, or for other fluids.
  e) A portable pH-meter for pH determination.
  f) Some metallic catheters for urine extraction, into a metallic case containing a disinfectant solution.
  g) Diverse instruments for cattle handling and tubes introduction as: a noser-holder, a mouth-wedge, etc.
  h) A portable case with reagents for both ruminal fluid and urine analyses.
  i) A videocassette with instructions (for collecting and analyzing ruminal fluid and urine, for the treatment of ruminal disorders).

Therefore it is an objective of the present invention to present an equipment of single usage, and easy for transportation, for the analyses of ruminal fluid and urine, with which veterinarians could perform the diagnosis at the field level of a total of sixteen different ruminants' diseases.

7 Claims, 10 Drawing Sheets

U.S. PATENT DOCUMENTS

| | | | |
|---|---|---|---|
| 5,380,525 | | 1/1995 | Leedle et al. .................. 424/93.4 |
| 5,503,112 | * | 4/1996 | Luhman et al. ................. 119/174 |
| 5,697,326 | * | 12/1997 | Mottram et al. ................. 119/174 |

FOREIGN PATENT DOCUMENTS

| | | |
|---|---|---|
| 1019516 | 12/1991 | (ES) . |
| 2634633 | 2/1990 | (FR) . |
| 2056944 | 3/1996 | (RU) . |

OTHER PUBLICATIONS

Geihauser, Thomas "An Instrument of Collection and Transfer of Ruminal Fluid and for Administration of Water Soluble Drugs in Adult Cattle." The Bovine Practitioner, No. 27, (Sep. 1993) pp. 38–42.

Howard, Jimmy L. "Ruminal Metabolic Acidosis." The Bovine Practioner, No. 16(Nov. 1981) pp. 44–53.

Nordlund, Kenneth, et al. "Herd–Based Rumenocentesis: A Clinical Approach to the Diagnosis of Subacute Rumen Acidosis." The Compendium Aug. 1995, S48 Food Animal, (8 pages).

Roussel, Allen J., et al. "Interpreting a Bovine Serum Chemistry Profile: Part 1." Veterinary Medicine, (Jun. 1997) pp. 553–566.

Nocek, James E. "Bovine Acidosis: Implications on Laminitis." Journal of Dairy Science, vol. 80, No. 5 (1997) pp. 1005–1028.

Oetzel, G.R., et al. "Screening of Anionic Salts for Palatability, Effects on Acid–Base Status, and Urinary Calcium Excretion in Dairy Cows." Journal of Dairy Science, vol. 74, No. 3 (1991) pp. 965–971.

Uribe, H.A., et al. "Genetic Parameters for Common Health Disorders of Holstein Cows." Journal of Dairy Science, vol. 78, No. 2 (1995) pp. 421–430.

Abstract of Grohn, Y.T., et al. "Epidemiology of Reproductive Disorders in Dairy Cattle: Associations among Host Characteristics, Disease and Production." Preventive Veterinary Medicine, vol. 8, No. 1 (1990) pp. 25–39.

Abstract of Nocek, J.E. "Bovine Acidosis: Implications on Laminitis." Journal of Dairy Science, vol. 80, No. 5 (May 1997) pp. 1005–1028.

Abstract of Nordlund, K.V., et al. "Herd–Based Rumenocentesis: A Clinical Approach to the Diagnosis of Subacute Rumen Acidosis." Food–Animal–Medicine–and–Management, vol. 17, No. 8 (1995) pp. s48–s56.

Abstract of Tanwar, R.K., et al. "Biochemical and microbial changes in experimentally induced rumen acidosis in goats." Indian Journal of Animal Science, vol. 53, No. 3 (1983) pp. 271–274 (Record 3 of 12).

Abstract of Moore, J.N., et al. "Equine Endotoxemia: An Insight Into Cause and Treatment." Journal of American Veterinary Medical Association, vol. 179, No. 5 (1981) pp. 473–477 (Record 4 of 12).

Abstract of Mount, M.E., et al. "Diagnostic Criteria for Carbaryl Poisoning in Sheep." Arch. Environ. Contam. Toxicol., vol. 10, No. 4 (1981) pp. 483–495 (Record 5 of 12).

Abstract of Hartmann, V.H., et al. "Pathogenesis of Calf Diarrhoea with Conclusions for Dietary Action." Monatsh. Veterinarmed, vol. 36, No. 10 (1981) pp. 371–377 (Record 7 of 12).

Abstract of Boyd, J.W. "Relationships between acid–base balance, serum composition and colostrum absorption in newborn calves." Br. Vet. J., vol. 145, No. 3 (1989) pp. 249–256 (Record 8 of 12).

Abstract of Naylor, J.M., et al. "Relationships between metabolic changes and clinical signs in pregnant sheep given endotoxin." Can. J. Vet. Res., vol. 50, No. 3 (1986) pp. 402–409 (Record 9 of 12).

Abstract of Oetzel, G.R., et al. "Screening of anionic salts for palatability, effects on acid–base status, and urinary calcium excretion in dairy cows." Journal of Dairy Science, vol. 74, No. 3 (1991) pp. 965–971 (Record 10 of 12).

Abstract of Andersson, B., et al. "Effects of hay–feeding on acid/base balance, renal sodium excretion, aldosterone and vasopressin secretion in the goat." Acta Physiol. Scand., vol. 126, No. 1 (1986) pp. 9–14 (Record 11 of 12).

Abstract of Ahuja, A.K., et al. "Efficacy of monensin on lactate production from in–vitro fermentation of starch." Indian Journal of Animal Science, vol. 59, No. 9 (1989) pp. 1054–1057 (Record 12 of 12).

Abstract of Auer, D.E., et al. "Illness in Horses following Spraying with Amitraz." Aust. Vet. J., vol. 61, No. 8 (1984) pp 257–259 (Record 6 of 12).

* cited by examiner

PORTABLE EQUIPMENT FOR OBTAINING AND ANALYZING RUMINAL LIQUID AND URINE

BACKGROUND OF THE EQUIPMENT

Ruminal and metabolic diseases of ruminants are very often presented in cows. Most of these diseases are developed in a subclinical form without manifesting evident clinical signs. That means the affected animals are found in an apparent good health-state, nevertheless the production may be decreased from 10 to 30%, without the owner's nor the veterinarians' awareness regarding that. As a rule, the first biochemical changes in the sick animal are presented in both the ruminal fluid and urine in a higher degree than in the blood, by this reason it is possible for the determination of them in the field conditions to use a single equipment that is of a very low cost.

Taking as a base the clinical record, the physical examination of the animals and the performing of single analyses in ruminal fluid and urine, veterinarians may diagnose most of these diseases in the practice, without requiring the sending of samples to the referral laboratories. Both metabolic and ruminal diseases (in a subclinical form), could be diagnosed in the field conditions with the proposed equipment.

With this equipment veterinarians will be able to diagnose in a different way sixteen different diseases in cattle, sheep and goats, using for this purpose just a very short time (from 15 to 20 minutes only).

Among the diseases which reference is made to, there are chronic ruminal acidosis, acute ruminal acidosis, acute ruminal alkalosis, chronic ruminal alkalosis, simple indigestion, putrefaction of ruminal content, intoxication by urea, ketosis, hepatic steatosis, left displacement of abomasum, right displacement of abomasum, ruminal microflora insufficiency in calves, dysfunction of esophageal groove in calves, abomasum dilatation and right displacement of abomasum in calves, left displacement of abomasum in calves and diverse inflammatory processes on the different animal species. The treatments that may be performed with the help of this equipment consist firstly in ruminal fluid taking (from 5 to 10 liters) from a healthy cow and the subsequent applying of the same to a sick cow, specially during diverse diseases as are the ruminal diseases, ketosis, hepatic steatosis, intoxication, toxemies and anorexia in general. In this way both bacteria and protozoa from the healthy cow are applied to the sick one in a treatment practically without cost. The equipment is also useful for the treatment on other kind of ruminal species as well as for the control and optimization of feeding rations; through its utilization it is possible to perform the diagnosis and prevention of:

1. Sixteen different metabolic diseases, both clinical and subclinical ruminal disorders on real field conditions, into a lapse from 15 to 20 minutes, may be diagnosed.
2. It is possible to prevent the presence of metabolic diseases, ruminal disorders and related diseases (mastitis, disorders of reproductive apparatus, infectious diseases, low immunity and viability, and diarrhoea in calves).
3. With the increase on the production and quality (of milk and meat) it is possible to lengthen the productive span of life of cows.
4. The mortality percentage of ruminants it is diminished, that implies a great economic advantage if it is considered that out of the 34 million bovines with which Mexico accounts, approximately 27 million are addressed to meet production, 3.5 million to milk production and the remaining to other kind of purposes.

Authors as Paasch, M. L. et al. (1994) meat mention about the frequency of subclinical ruminal acidosis found in dairy cows with high production is 36%, and 16% with standard production. We may say that approximately 140 000 dairy cows suffer from ruminal acidosis in a subclinical form, only out of 700 000 cows with high production.

Along the course of this disease the milk production of the cow may become diminished from 10% to 30%, which is equivalent to an average of 3 liters per cow per day.

The annual diminution in cows with high production in Mexico due to subclinical ruminal acidosis, has been evaluated in 50 400 000 liters of milk (without accounting neither the losses caused on milk quality nor the losses caused by the diverse related diseases: affections of the reproductive apparatus, rumenitis-hepatitis, mastitis). On the other hand it has not been possible to determine the losses caused by other metabolic diseases such as ketosis, ruminal alkalosis, among others, but it is possible that these losses might be higher than those due to subclinical ruminal acidosis.

In beef cattle (27 million animals) the economic losses are higher and more important than in dairy cows, however the frequency of metabolic and ruminal diseases in beef cows it is unknown.

Most of the metabolic diseases and ruminal disorders in sheep and goats (approximately 18 million animals) may be diagnosed, treated and prevented with our equipment. Both ruminal disorders and the economic advantage of the usage of our equipment for diagnosis, treatment and prevention of metabolic diseases are very important, not only for the health of the animals but also for the production systems' economy.

BRIEF DESCRIPTION OF FIGURES

FIG. 8. It corresponds to the collection (8A) and to the applying (8B) of ruminal fluid.

FIG. 9. It corresponds to the checking of the correct position of the ruminal tube (9A) and to the ruminal fluid obtention (9B).

DETAILED DESCRIPTION OF THE EQUIPMENT

The device is referred to as a portable equipment for obtaining and analyzing the ruminal fluid and urine (FIGS.

1,2 and 5), therefore the equipment is designed for easily obtaining these fluids with the aim of performing a fast diagnosis in practice (FIGS. 1 and 2), besides of make a safe and fast applying of the ruminal fluid from a healthy animal to a sick one (FIGS. 8A and 8B), as well as for providing other fluids and drugs to the rumen. The rumen washings and also ruminal fluid extractions may be performed along with surgical actions and treatments, inclusive on horses with gastric dilatation.

Following the equipment and its performing is described:

1. Collection of Ruminal Fluid with the Aid of the Suction Pump

Figure 1:
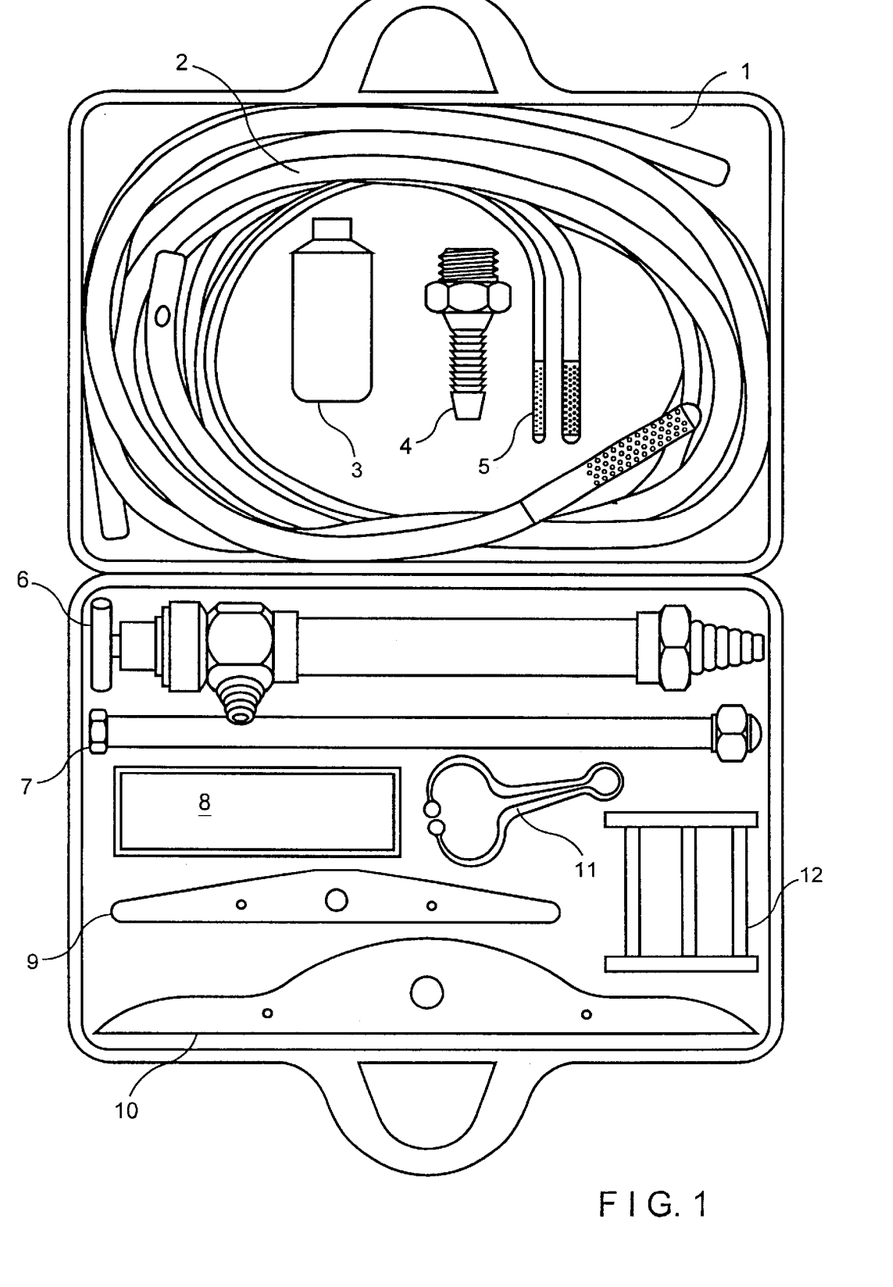
FIG. 1. It corresponds to an illustration of the case containing the different instruments conforming the equipment.
Figure 6:
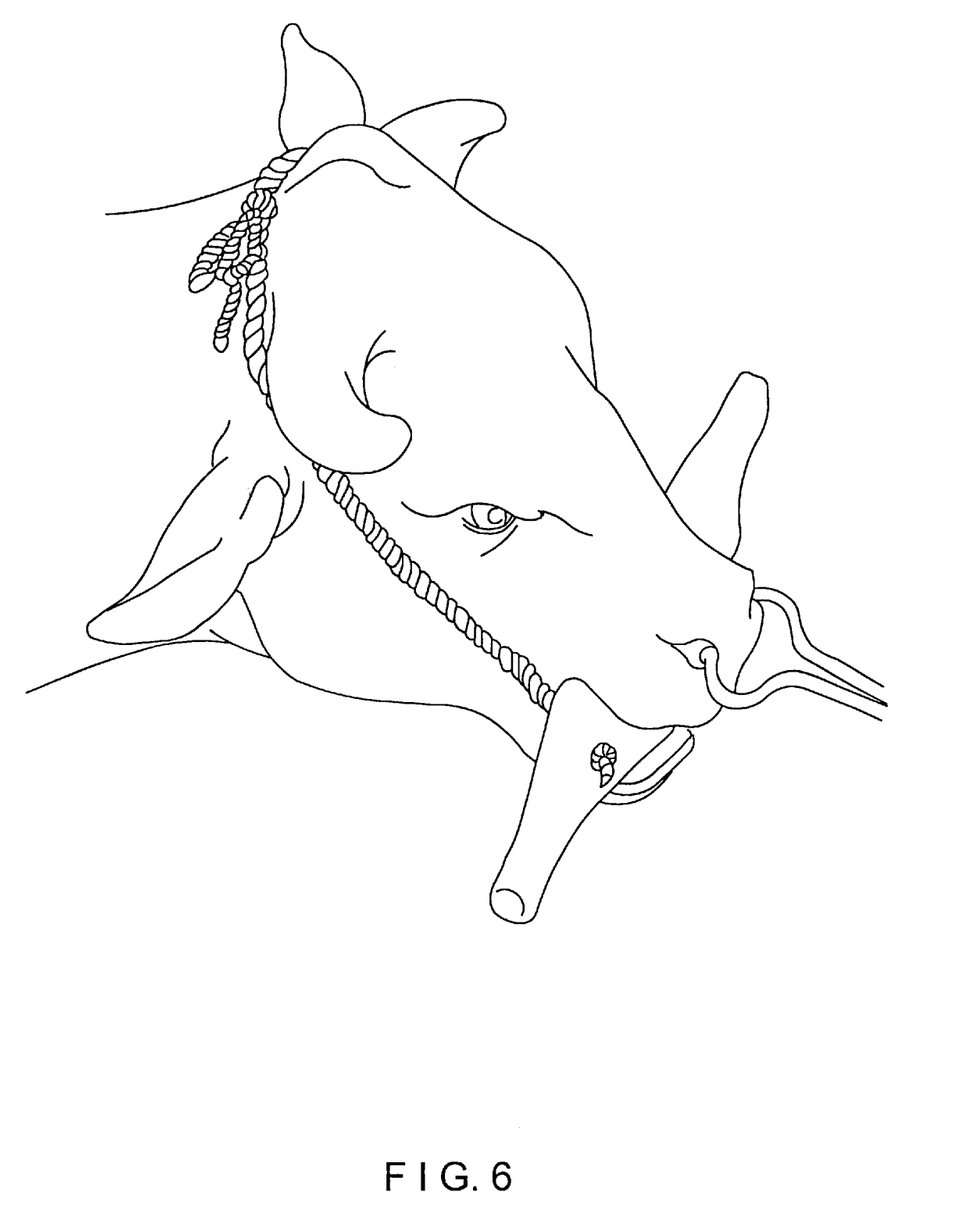
FIG. 6. It corresponds to the subjection technique for the animal handling for applying the mouth-wedge.
Figure 7:
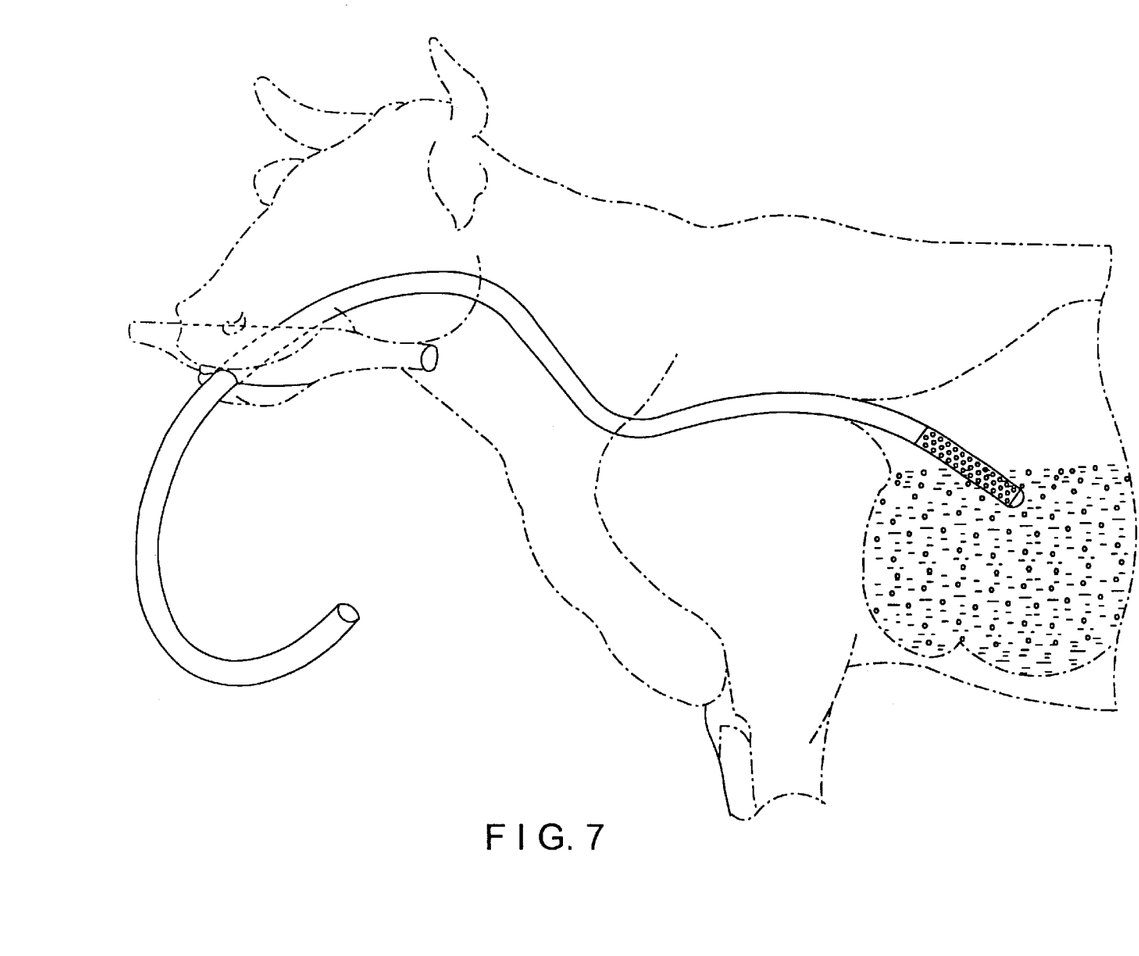
FIG. 7. It corresponds to the introduction of the ruminal tube into the rumen.
Figure 8A:
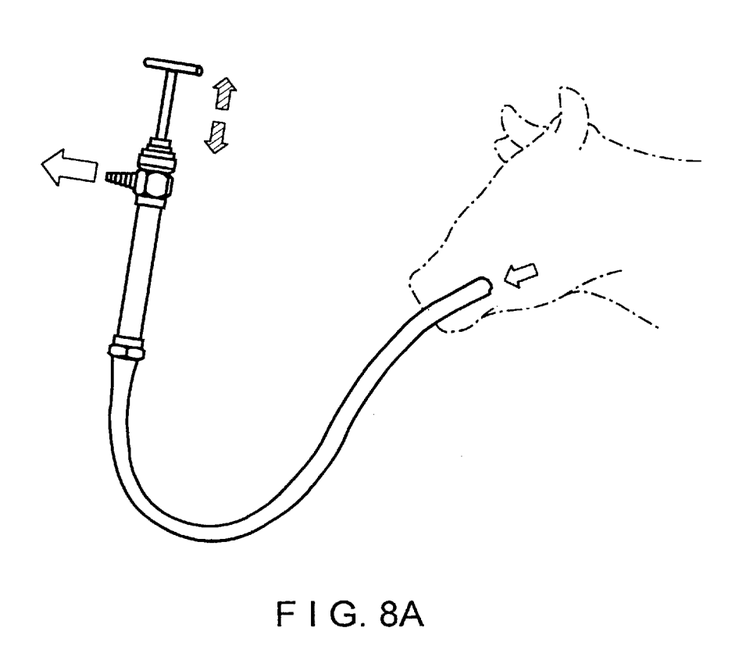

With the aid of the nose-holder the animal is secured (FIG. 1,11) for subsequently applying to the same the mouth-wedge (FIG. 1,10) by tying on the belts to the horns or to the neck of the animal (FIG. 6). The ruminal tube with metallic head having 3 mm diameter perforations for avoiding obstructions (FIG. 1,1) is lubricated with water and is introduced through the mouth-wedge into the rumen (FIG. 7). Once the ruminal tube is introduced, a portion of approximately one meter of the ruminal tube should remain outside the animal, in a free manner; this obviously depending upon the animal size. The free end of the ruminal tube is connected out to the suction pump (FIG. 1,6) in its distant end. This suction pump has a funnel structure, by means of which different diameters ruminal tubes may be coupled to. Subsequently, a nasoesophageal tube for horse is connected to the lower connection of the suction pump for the collection of the ruminal fluid into a plastic recipient (FIG. 1,3). For the good performance of the suction pump, it is necessary the suction pump remains in a vertical position; and to avoid the salivary influence approximately the first 50 ml of the extracted ruminal fluid should be eliminated (FIG. 8A). The ruminal fluid obtained should be stored transiently in a plastic recipient, (FIG. 1,3) for its subsequent analysis.

In case of obstruction of the ruminal tube, it will be sufficient to move it frequently with inward and outward movements, to facilitate the ruminal fluid extraction. In some illnesses, as in the putrefaction of the ruminal content, the ruminal fluid's viscosity is increased; reason by which it will be necessary to apply from 3 to 5 liters of water and to provide abdominal massage from the outside for the ruminal fluid to be diluted. Having accomplished the procedure it will be necessary to put special care when removing the ruminal tube from the rumen to avoid the vacuum that could impair the esophagus' mucose.

2. Ruminal Fluid Extraction with the Aid of a Milking Machine

With this method, it is possible to obtain great amounts of ruminal fluid for the treatment of ruminal disorders. The components for this extraction form are: ruminal tube with metallic head having 3 mm diameter perforations for avoiding obstructions (FIG. 1,1), metallic collection tank (FIG. 3), nasoesophageal tube for horse (FIG. 1,2) and connection for the milking machine (FIG. 1,4). The type of adapter will depend upon the type of the milking machine to be used.

Figure 10:
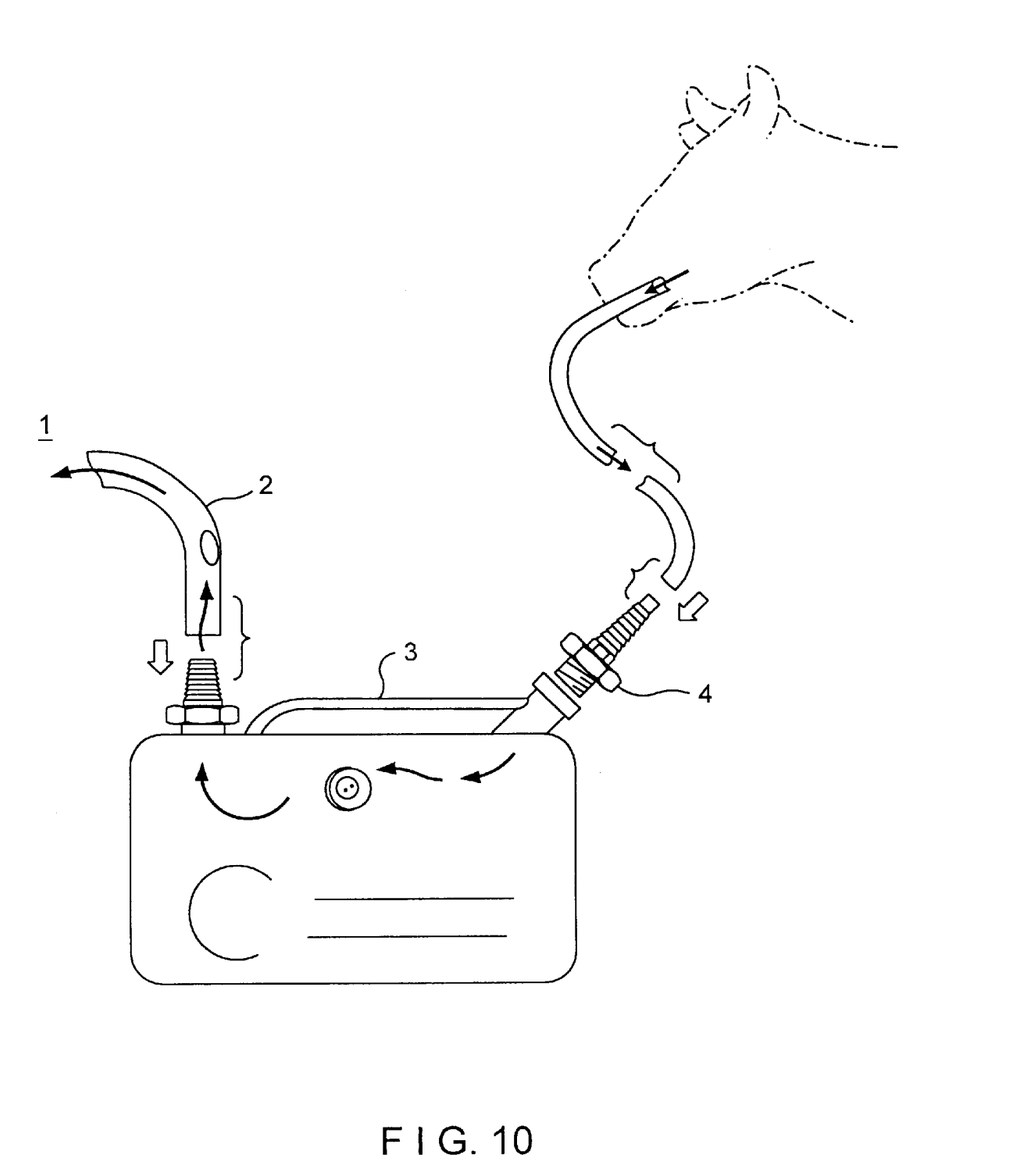
FIG. 10. It corresponds to the ruminal fluid obtention from a healthy animal, using the, collection tank.

One end of the nasoesophageal tube for horse (FIG. 1,2) is connected to the milking machine connection, while the opposite end (which may be identified by the presence of a side hole) is connected to the collection tank, (FIG. 10,1). The ruminal tube is introduced into the rumen as yet was described previously in a manner that the other end be communicated with the collection tank (FIG. 10,4). The connection for the milking machine is connected to the milking machine and the later is activated. For vacuum generation into the collection tank, the perforation of the nasoesophageal tube for horse is obstructed (FIG. 10,2) with the aid of a finger. In this way vacuum is produced into the collection tank, at the same time the suction on the ruminal fluid will be produced, dragging it inward the collection tank. For ruminal fluid level checking, and avoiding the ruminal fluid passage into the milking machine, the collection tank is equiped with sided small windows (FIG. 10,3). In a few minutes there will be collected some liters of ruminal fluid, with the equipment and the procedure, it is possible to obtain, from 4 to 10 liters of ruminal fluid.

3. Applying Ruminal Fluid from a Healthy Cow for Therapeutic Purposes

Once from 4 to 10 liters of ruminal fluid have been obtained from a healthy cow, the ruminal tube is introduced into the rumen of the sick cow.

Figure 9A:
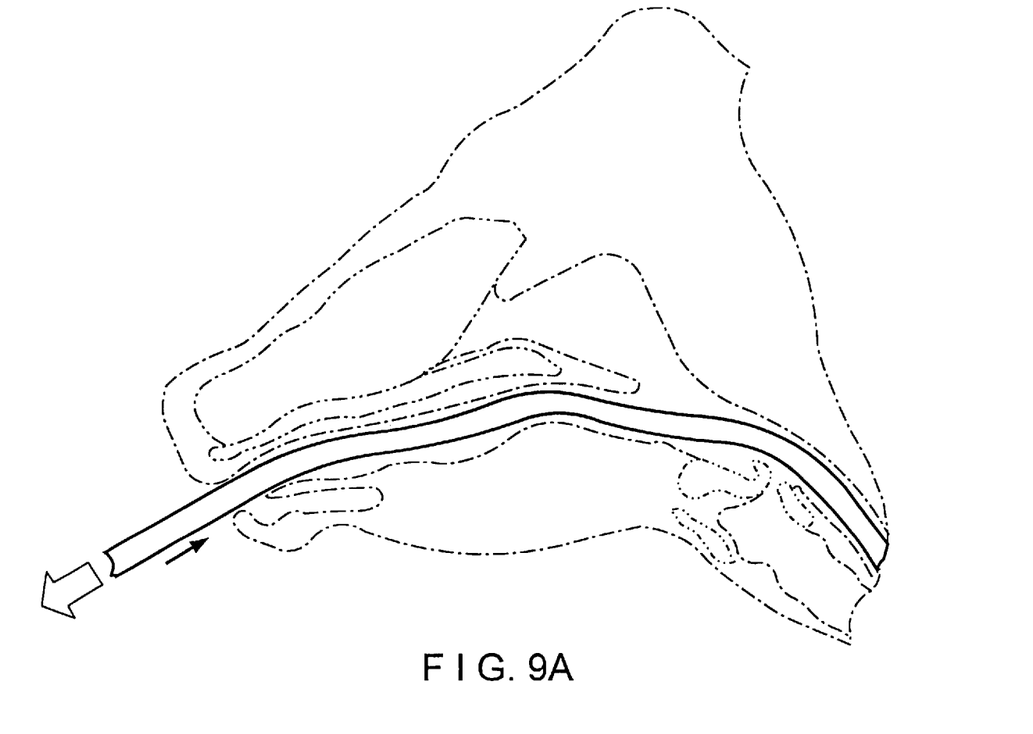
Figure 9B:
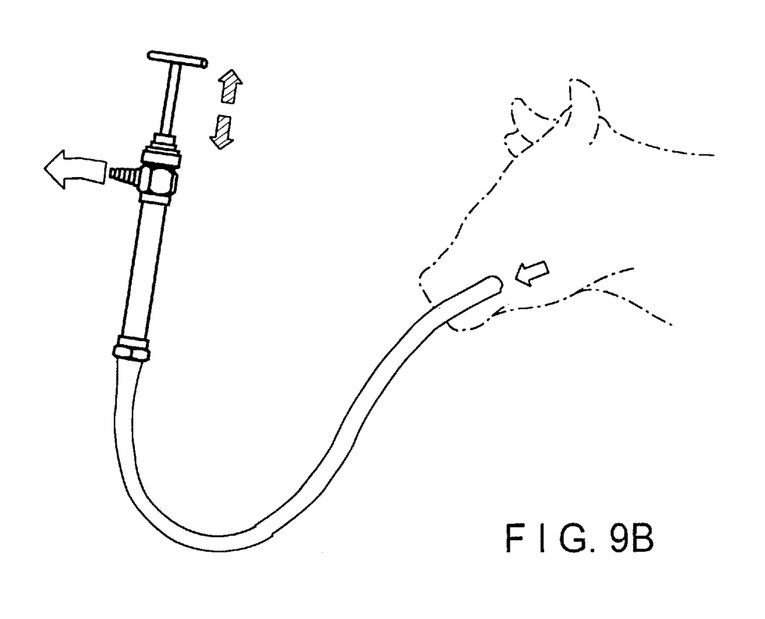

To confirm the ruminal tube introduction has been adequately performed, it is observed an increase in size in the left yugular groove as the ruminal tube end goes down; another way of checking may be through the perception of the characteristic odor expelled by the ruminal tube (FIG. 9A), or well, the ruminal tube will produce bubbles, if the end is submerged into a pail with water, in the case the tubing had been erroneously performed. Another way of checking the ruminal tube setting is on the correct place is through the applying of 300 ml of water, so that if the ruminal tube was introduced into the respiratory way the animal would cough immediately. Of course the easiest and unequivocal manner will be to obtain a little amount of ruminal content (FIG. 9B).

The ruminal fluid will be provided into the rumen, connecting the ruminal tube coming from the animal to the collection tank (FIGS. 3 and 10,3) and this is raised so that the ruminal fluid passes by gravity easily. If the passing of the ruminal fluid become difficult it will be necessary to move the ruminal tube, but if it otherwise become completely obstructed it may be possible to remove the obstruction through the circulation of current water with the suction pump (FIGS. 1,6 and 8B) for the obstruction removing.

The same procedure is valid for applying other solutions and drugs to be provided. It is very important to remember that when the ruminal tube is removed it should be avoided the vacuum generation so that the impairment of the rumen or of the esophagus' mucose do not to be produced. The esophagus' spasmous when the removing of the ruminal tube is only very seldom produced, however to these cases it will be possible the ruminal tube removing with soft inward and outward movements. When regurgitation is presented during the applying of ruminal fluid, the procedure should be stopped and the head of the animal should be put to the ground to prevent the possible aspiration of the content to the lungs.

4. Washing of the Rumen

This procedure is indicated for acute ruminal acidosis, of putrefaction of the ruminal content cases, or in feeding intoxication cases.

Figure 4:
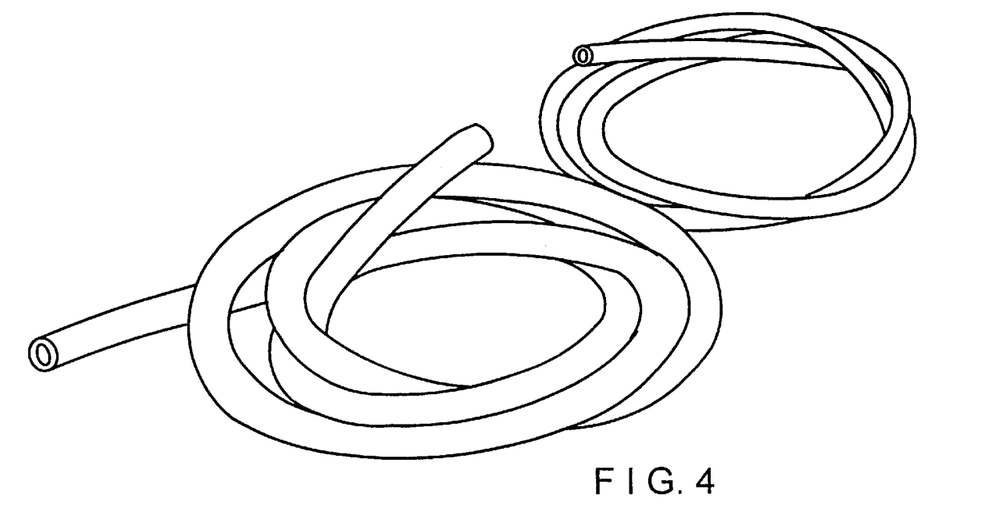
FIG. 4. It corresponds to an illustration of the ruminal tube for washing the rumen, as well as some replacement hoses.

With the aid of the mouth-wedge is introduced into the rumen (FIG. 4) a rubber tube of approximately 32 mm diameter. It may be possible also to use the ruminal tube with metal head, and for this a portion of a ruminal tube is introduced in a manner such that the metal head remains outside without its end-cap.

Figure 3:
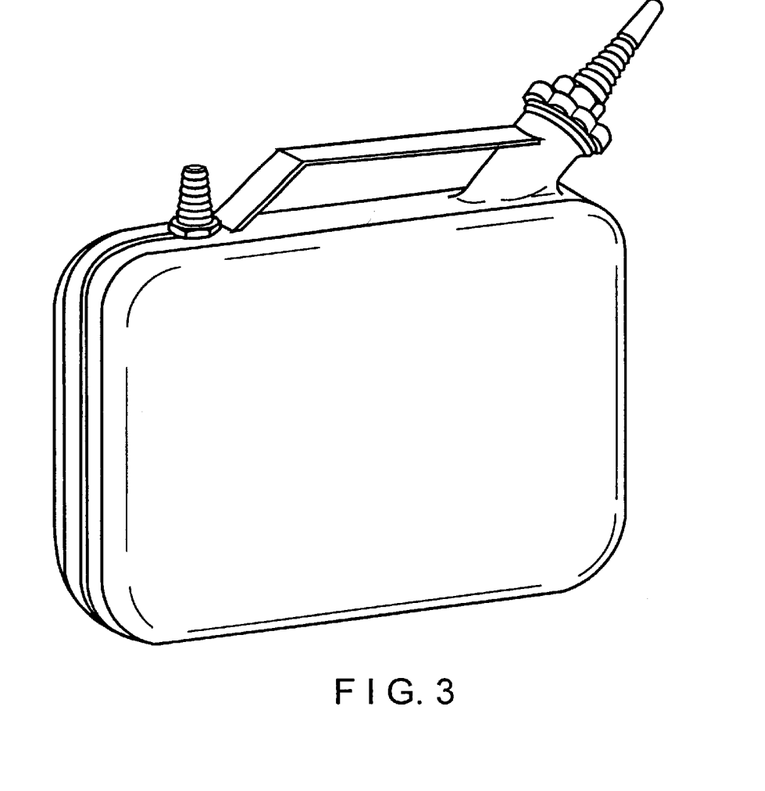
FIG. 3. It corresponds to an illustration of the collection tank of fluids.
Figure 8B:
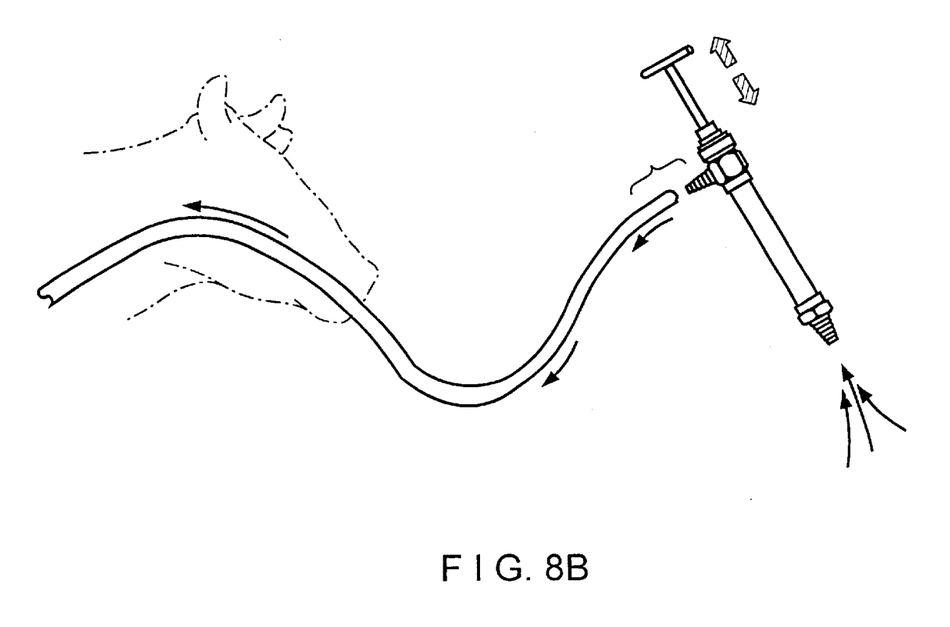

Because of the fact that in acute acidosis the rumen content is fluid, its removing is particularly easy if the cow is laying down in a lateral position, with the elimination practically spontaneous of the content. If it is not so, for its extraction the suction pump usage will be required, and the collection tank utilization will be desirable (FIGS. 3 and 10). After elimination of the abnormal ruminal fluid, with the aid of the suction pump through the collection tank, 30 liters of water are applied, giving subsequently massage to the rumen to mix the water with the rumen content. The procedure should be repeated at least three additional times (FIGS. 8A and 8B).

5. Collection of Urine in Cows through Catheterization of Urinary Bladder

Urine collection and its subsequent analysis should be considered as an important part in the diagnosis of a wide set of pathologies.

Figure 11A:
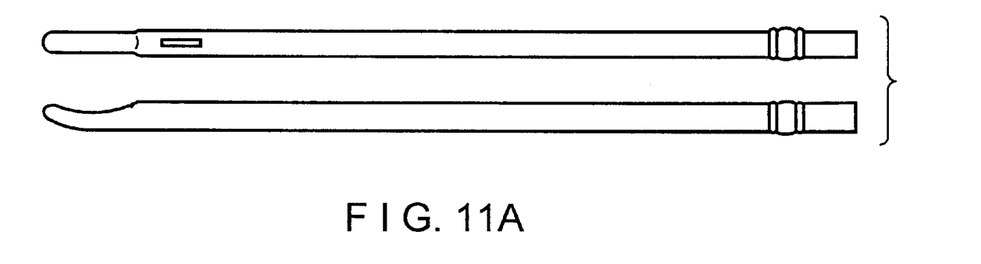
FIG. 11. It corresponds to the technique for urine obtention.
Figure 11B:
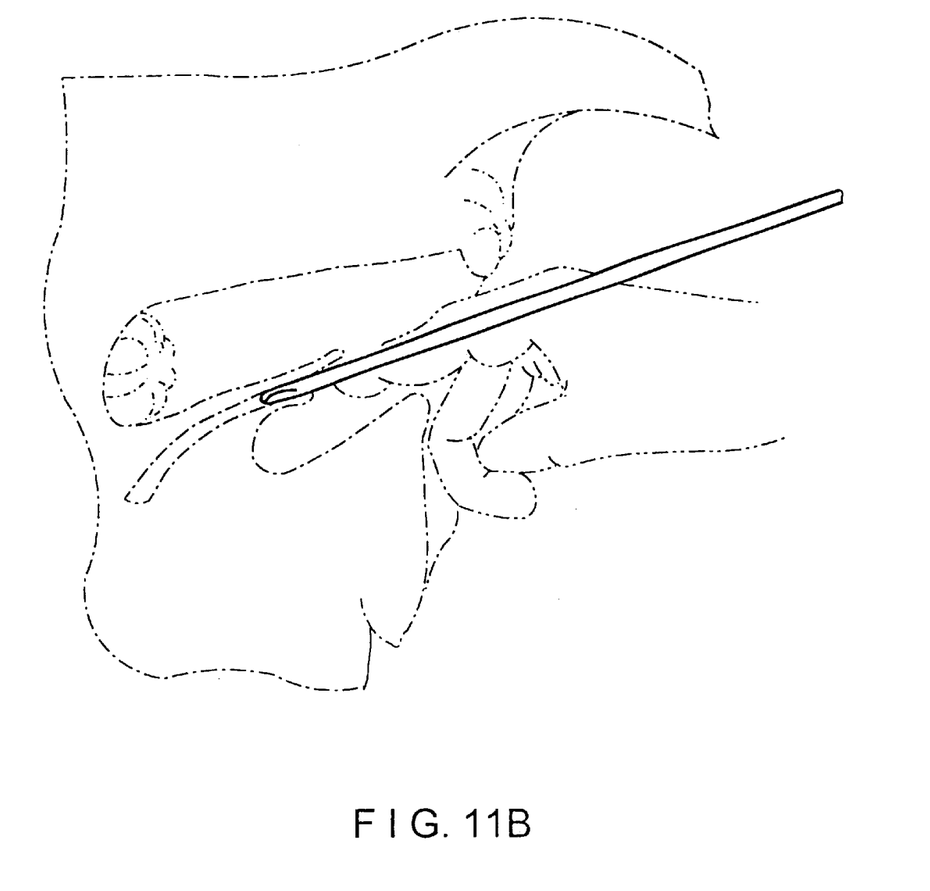

The metallic catheters used (FIGS. 1,7 and 11A) should be previously maintained into a disinfectant solution.

For proceeding with the sample taking, the vulva should be cleaned (previously washed), dried and disinfected.

After the catheter is extracted from the case, it should be rinsed out both internally and externally with distilated water, to avoid the influence of the disinfectant when analyzing the sample.

The catheter is introduced into the urinary bladder collecting the urine into a plastic bottle.

In the case that difficulties arise at the moment of the urine sample taking, it is permissible for overcoming them, to move the catheter with subtle inward-and-outward movements, or well, through insulation with the air of a syringe or with a pear-shape air-blower.

6. Equipment Maintenance

Once the maneuvers with the equipment are accomplished, it should be both internally and externally washed out, drying it finally with a clean cloth.

Figure 2:
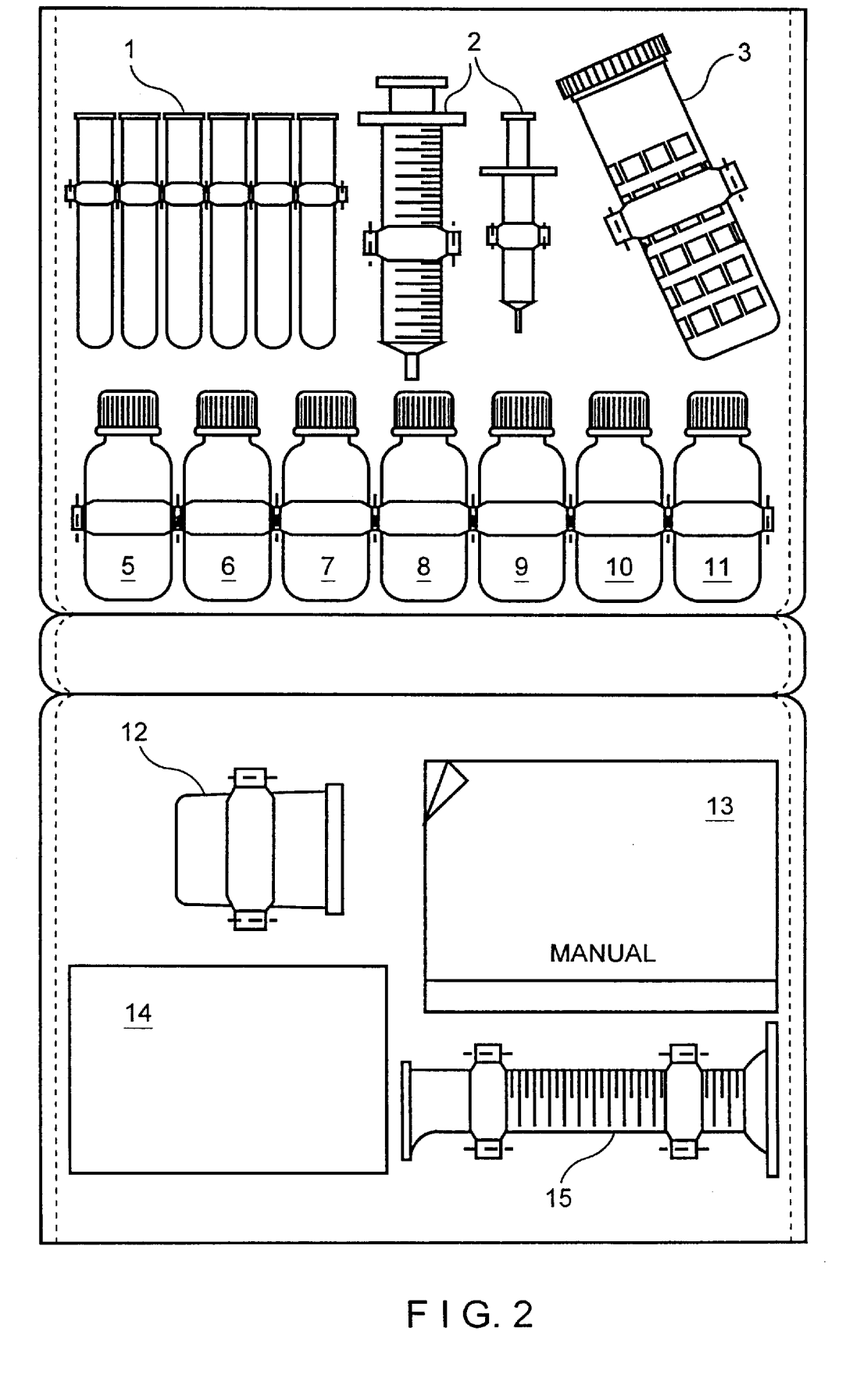
FIG. 2. It corresponds to an illustration of the reagents' case, for performing the analyses of the ruminal fluid and urine. Besides of containing a demonstrative videocassette of the equipment usage and an instructive handbook for the proper usage of the case.

The suction pump should be fall to pieces (felt apart) for making possible to wash out with water each of its components, drying them subsequently with a clean cloth. It is also pertinent the usage of a disinfectant solution and then the rinsing with clean water. Finally vaseline will be applied to the rubber piston for maintaining its elasticity and lubrication (FIG. 2,12). If the rubber piston were impaired it would be pertinent to replace it immediately to optimize the good performing of the equipment. The collection tank should be perfectly washed out and always to remain clean taken care about the ruminal fluid level control sidewindows also remain clean to allow the level visibility in future situations.

7. Ruminal Fluid Examination

Previous to the ruminal fluid analysis, the ruminal fluid should be shaken to homogenize it.

For observing its physical features, such as color, odor, consistency, flotation and sedimentation; from 30 to 50 ml ruminal fluid are placed into a calibrated cylinder (FIG. 2,15). It should be taken into consideration that the normal ruminal fluid sedimentation and flotation lapse is about 8 minutes.

To assess the reductive activity, 0.5 ml of 0.03% methylene blue solution (FIG. 2,8) are placed into a test tube (FIG. 2,1), then, 10 ml ruminal fluid are added to, and mixed with. Subsequently, using a second test tube called "control", only 10 ml ruminal fluid is placed into it.

The interpretation of the assay described above is in a normal ruminal fluid there will be decoloration in a 3 to 6 minutes-lapse after adding the stain aggregate, producing an approximately 2 mm thickness ring in the top section of the test tube.

8. Determination of pH

Because of pH determination is one of the most important parts in the ruminal fluid analyses, it will be of great usefulness a portable pH-meter (FIG. 1,8).

The electrode's cap is removed and the pH-meter is calibrated using a 4.0 pH buffer solution from 30 to 60 seconds (FIG. 2,5). If the pH-meter does not indicate a 4.0 pH, the pH-meter should be accurately adjusted with the aid of a screwdriver.

Subsequently, the electrode is washed out with distilated water or faucet water and is introduced into a second recipient which contains a 7.0 pH buffer solution (FIG. 2,7). Seemingly, if the pH-meter does not indicate a 7.0 pH, it should be calibrated with the aid of a screwdriver. The electrode is washed out with faucet water, and then it is, when ready to be used to measure the ruminal fluid pH.

For the correct reading, the pH-meter will be put in contact with the ruminal fluid during 30–60 seconds. After the reading, the electrode is washed out, and for it to remain wet faucet water is placed into the electrode cap. When diverse samples are evaluated it is necesary to calibrate the pH-meter again.

9. Urine Analysis

Physical examination of urine: In a test tube (FIG. 2,1) some of the urine's physical features such as color, odor, and sedimentation are assesed. For protein presence determination, on the ruminant's urine or well on the herbivores' urine, it is not completely satisfactory the usage of the reactive strips (FIG. 2,3), reason by which it will be necessary recurring to the usage of sulfosalicylic acid at 20% as a reactive (FIG. 2,9).

Figure 5:
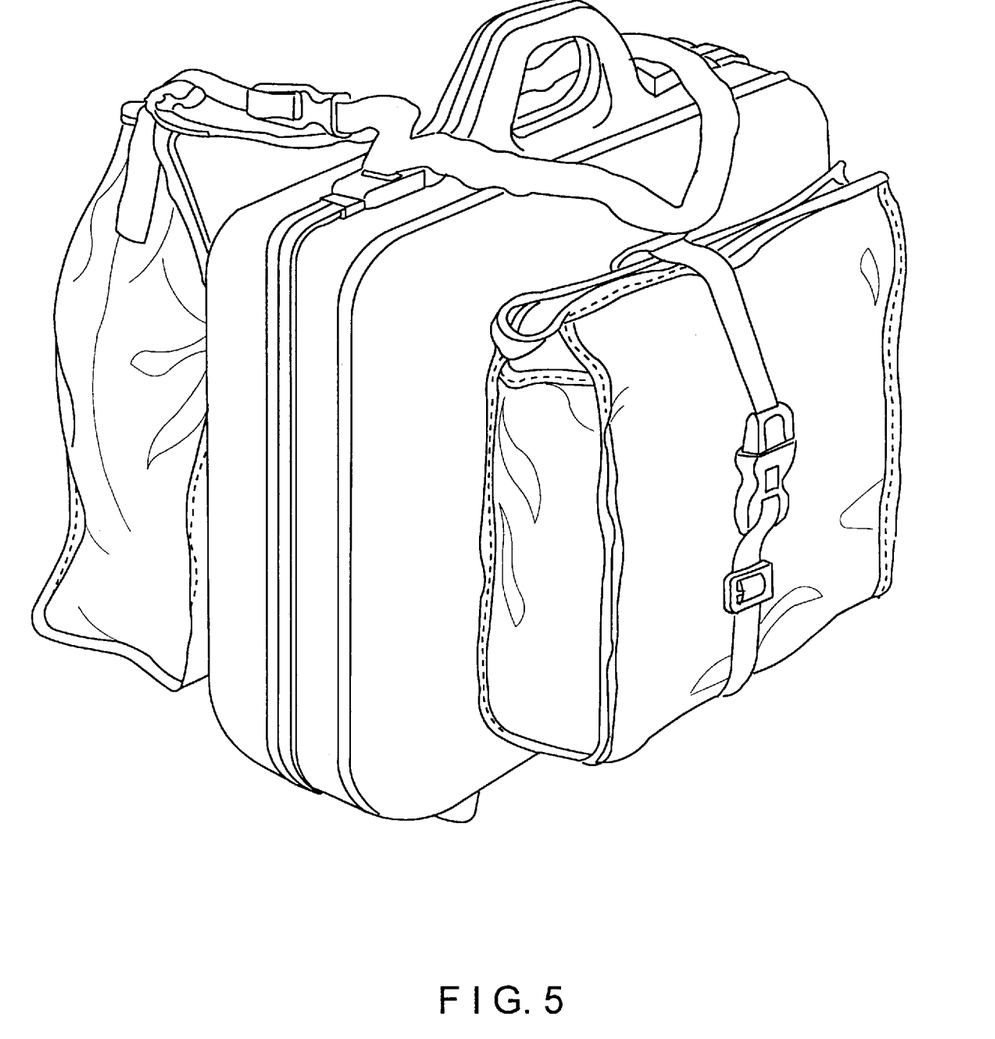
FIG. 5. It corresponds to an illustration of the complete case, into which the different instruments, reagents and the collection tank of fluids, are all included.

5 ml urine are placed into each of two test tubes being the first tube the test-one and the other the control tube. One ml sulfosalicylic acid at 20% solution is placed into the problem tube (FIG. 2,9), with the aim of assesing the existent turbidness grade, in case of the presence of protein in urine. In a similar manner, as that described for the ruminal fluid, the pH-meter is used to asses urine pH (FIG. 1,8). One time the study is accomplished, the equipment, completely clean, should newly be set into the case (FIG. 5).

Following the procedure described here above, from the first step to the ninth step, with the components of this equipment, the diagnosis could be done in a time lapse from 15 to 20 minutes. This diagnosis will be useful to modify an unbalanced diet due to the identification of unfavorable biochemical changes in the ruminants to prevent the development of metabolic disorders.

While invention has been particularly described and shown, this is regarded as a novelty.

What is claimed:

1. Portable equipment for obtaining and analyzing ruminal fluid and urine in the diagnosis of 16 diseases of ruminants, in a range from 15 to 20 minutes; the equipment design facilitating the collecting of ruminal fluid and urine; the equipment capable of being used by a single person; the ruminal fluid from a healthy cow capable of being introduced to a sick one; the equipment consisting of a single transportation case into which the following instruments are included: a) a ruminal tube with metallic head for collecting and introducing ruminal fluid as well as other fluids from adult bovines; b) a ruminal tube with metallic head for collecting and introducing ruminal fluid to calves and small ruminants; c) a double-way metallic suction pump for collecting and introducing ruminal fluid and other fluids; d) a five liters capacity collection tank for obtaining and introducing the ruminal fluid; e) a portable pH-meter for pH determination; f) metallic catheters for urine collection, placed into a metallic case containing a disinfectant solution; g) instruments for cattle handling, and for the introduction of ruminal or rubber tubes as a nose-holder, two mouth-wedges, used for the introduction of the ruminal tube into adult bovines as well as into small ruminants; h) a portable case with reagents which are used in the analysis of ruminal fluid and urine; i) a videocassette with instructions, for collecting and analyzing ruminal fluid and urine for the treatment of ruminal disorder; j) reagents.

2. A method for obtaining and analyzing ruminal fluid and urine in the diagnosis of diseases of ruminants with the portable equipment of claim 1, wherein from 4 to 10 liters of ruminal fluid are extracted from a healthy cow and then they are introduced to a sick one with the purpose that the ruminal content of the latter become normalized.

3. A method for obtaining and analyzing ruminal fluid and urine in the diagnosis of diseases of ruminants with the portable equipment of claim 1, wherein the diagnosis is performed in a range from 15 to 20 minutes under field conditions or in farms.

4. Portable equipment for obtaining and analyzing ruminal fluid and urine in the diagnosis of diseases of ruminants, in accordance with claim 1, wherein the head of the ruminal tube has 3 mm diameter perforations for avoiding obstructions.

5. A method for obtaining and analyzing ruminal fluid and urine in the diagnosis of diseases of ruminants with the portable equipment of claim 1, wherein for performing the urine analysis, 1 ml sulfosalicylic acid solution is added as a reactive to the urine.

6. Portable equipment for obtaining and analyzing ruminal fluid and urine in the diagnosis of diseases of ruminants, in accordance with claim 1, wherein the suction pump has a funnel structure which different diameter ruminal tubes may be coupled to.

7. A method for obtaining and analyzing ruminal fluid and urine in the diagnosis of diseases of ruminants with the portable equipment claim 1, wherein a quick diagnosis of biochemical changes in ruminal fluid and urine due to the unbalanced diets can be used to improve the feeding rations to prevent the metabolic disorders of ruminants.

* * * * *